United States Patent [19]
Brown et al.

[11] Patent Number: 5,422,118
[45] Date of Patent: Jun. 6, 1995

[54] TRANSDERMAL ADMINISTRATION OF AMINES WITH MINIMAL IRRITATION AND HIGH TRANSDERMAL FLUX RATE

[75] Inventors: Larry R. Brown, Newton, Mass.; John F. Cline, Westfield, N.J.; James Davidson, deceased, late of Brookline, Mass., by Betty Davidson, executrix

[73] Assignee: Pure Pac, Inc., Elizabeth, N.J.
[21] Appl. No.: 948,232
[22] Filed: Sep. 21, 1992

Related U.S. Application Data

[63] Continuation-in-part of Ser. No. 296,406, Jan. 9, 1989, abandoned, which is a continuation of Ser. No. 928,922, Nov. 7, 1986, abandoned.

[51] Int. Cl.$^6$ .................. A61F 13/00; A61K 9/08; A61K 31/13
[52] U.S. Cl. .................... 424/449; 514/947
[58] Field of Search ............ 424/449; 514/947
[56] References Cited

U.S. PATENT DOCUMENTS

| | | | |
|---|---|---|---|
| 2,693,438 | 11/1954 | Ward | 424/445 |
| 2,735,799 | 2/1956 | Abramson | 514/653 |
| 3,279,996 | 10/1966 | Long et al. | 424/424 |
| 3,287,222 | 11/1966 | Larde et al. | 424/445 |
| 3,304,230 | 2/1967 | Abramson et al. | 514/947 |
| 3,545,439 | 12/1970 | Duncan et al. | 424/432 |
| 3,598,123 | 8/1971 | Zaffaroni | 424/435 |
| 3,710,795 | 1/1973 | Higuchi et al. | 424/424 |
| 3,731,683 | 5/1973 | Zaffaroni | 424/426 |
| 3,734,097 | 5/1973 | Zaffaroni | 424/448 |
| 3,792,951 | 2/1974 | Meyers | 424/426 |
| 3,797,494 | 3/1974 | Zaffaroni | 424/448 |
| 3,946,106 | 3/1976 | Chien et al. | 424/425 |
| 3,992,518 | 11/1976 | Chien et al. | 424/425 |
| 3,996,934 | 12/1976 | Zaffaroni | 424/434 |
| 4,031,894 | 6/1977 | Urquhart et al. | 424/449 |
| 4,053,580 | 10/1977 | Chien et al. | 424/425 |
| 4,060,084 | 11/1977 | Chandrasekaran | |
| 4,210,633 | 7/1980 | Takrui et al. | 514/178 |
| 4,291,015 | 9/1981 | Keith et al. | 514/509 |
| 4,314,557 | 2/1982 | Chandrasekaran | 424/449 |
| 4,336,243 | 6/1982 | Sanvordeker et al. | 424/449 |
| 4,379,454 | 4/1983 | Campbell et al. | 424/448 |
| 4,458,990 | 7/1984 | Kawai | 359/700 |
| 4,460,371 | 7/1984 | Abber | 424/448 |
| 4,461,759 | 7/1984 | Dunn | 424/465 |
| 4,486,193 | 12/1984 | Shaw et al. | 424/449 |
| 4,690,683 | 9/1987 | Chien et al. | 604/896 |
| 4,716,497 | 12/1987 | Heller et al. | 514/947 |
| 4,751,087 | 6/1988 | Wick | 424/449 |

FOREIGN PATENT DOCUMENTS

| | | |
|---|---|---|
| 0013606 | 7/1980 | European Pat. Off. |
| 0262753 | 4/1988 | European Pat. Off. |
| 83/00091 | 1/1983 | WIPO |
| 86/00806 | 2/1986 | WIPO |

OTHER PUBLICATIONS

Black, C. D., "Update: Programmed Drug Delivery Systems," *U.S. Pharmacist*, Nov. 1983, pp. 49–60.

"New Systems for Drug Delivery: Targeted, Sustained Cost-Effective," *Chemical Week*, Sep. 26, 1984, pp. 42–46.

Chien, Y. W., "Logics of Transdermal Controlled Drug Administration," *Drug Development and Industrial Pharmacy*. vol. 9, No. 4, pp. 497–520 (1983).

"The Transderamal Nitroglycerin Therapeutic System", CIBA Pharmaceutical Company, Summit New Jersey.

Windheuser, J. J., et al., "The Use of N,N-Diethy-m-Toluamide to Enhance Dermal and Transdermal Delivery of Drugs," *J. Pharm. Sciences*, vol. 71, No. 11, (Nov. 1982) pp. 1211–1213.

"The New Transdermal Nitroglycerin 'Patches'," *American Pharmacy*, vol. NS22, No. 2, (1982).

Billups, N. E., *American Drug Index*, Billups, S., Assoc. Editor, 27th Edition, p. 652, (1983).

Michaels, A. S., et al., "Drug permeation through human skin: theory and in vitro experimental measurement," *A.I.Ch.E.J.*, (1975) vol. 21, 985–996.

*Primary Examiner*—Thurman K. Page
*Assistant Examiner*—Peter F. Kulkosky
*Attorney, Agent, or Firm*—Kilpatrick & Cody

[57] ABSTRACT

An effective amount of a skin irritating physiologically active amine can be transdermally or topically administered in a minimally or nonirritating composition that maintains a suitably high transdermal flux rate, by providing the amine as a minimally or nonirritating salt of a stoichiometric molar excess of a fatty acid of from 8 to 20 or 22 carbon atoms, in a nonpolar, nonvolatile solvent.

22 Claims, 6 Drawing Sheets

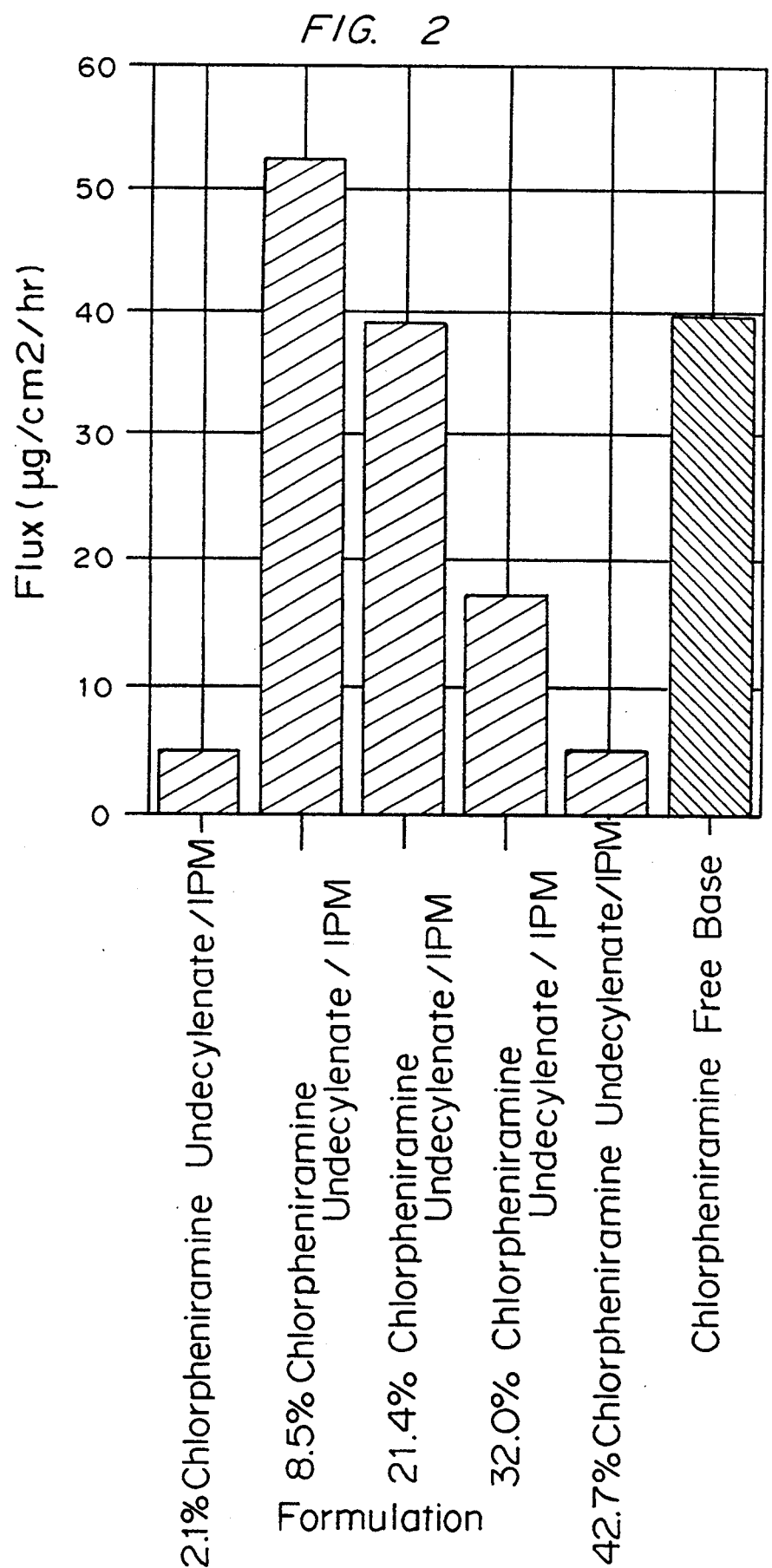

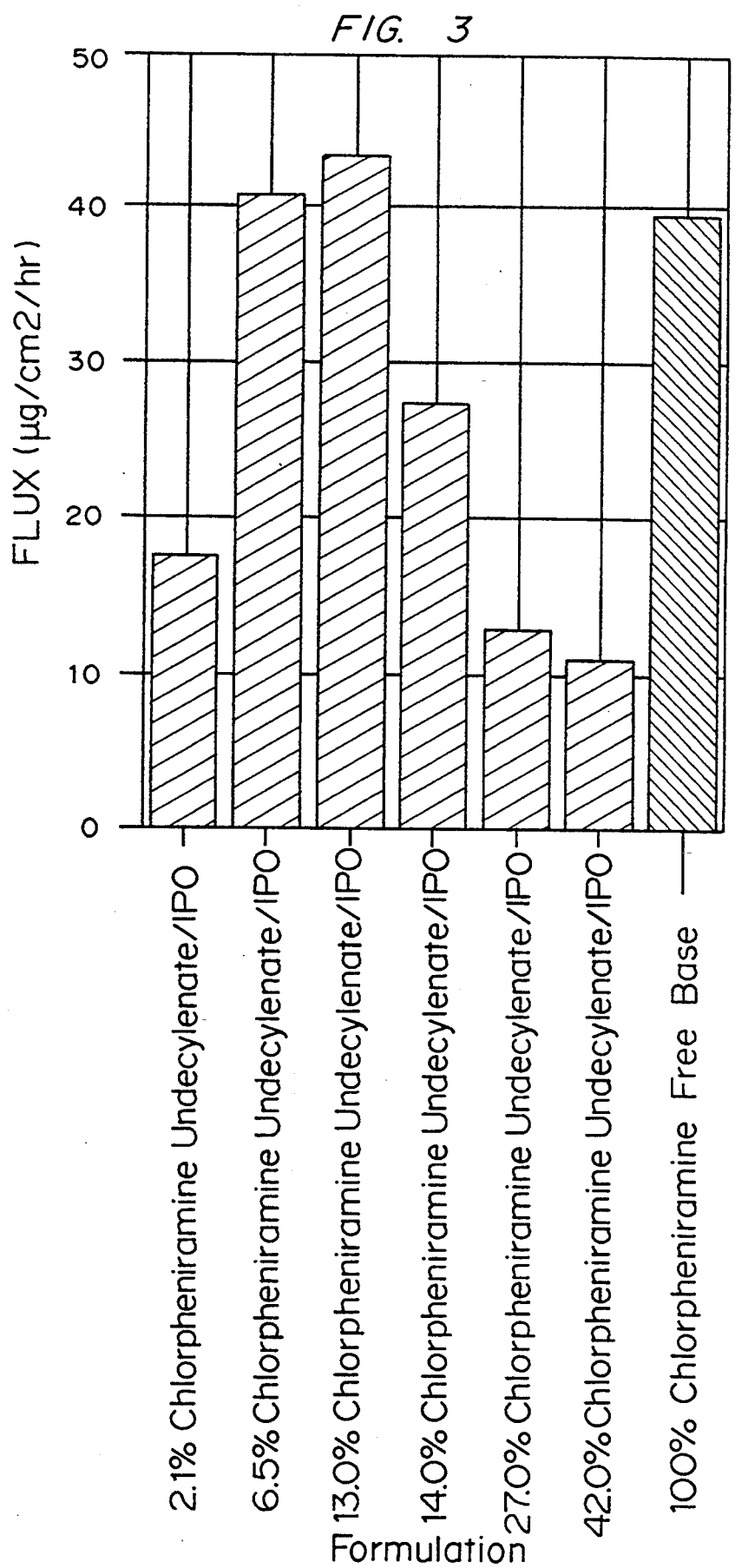

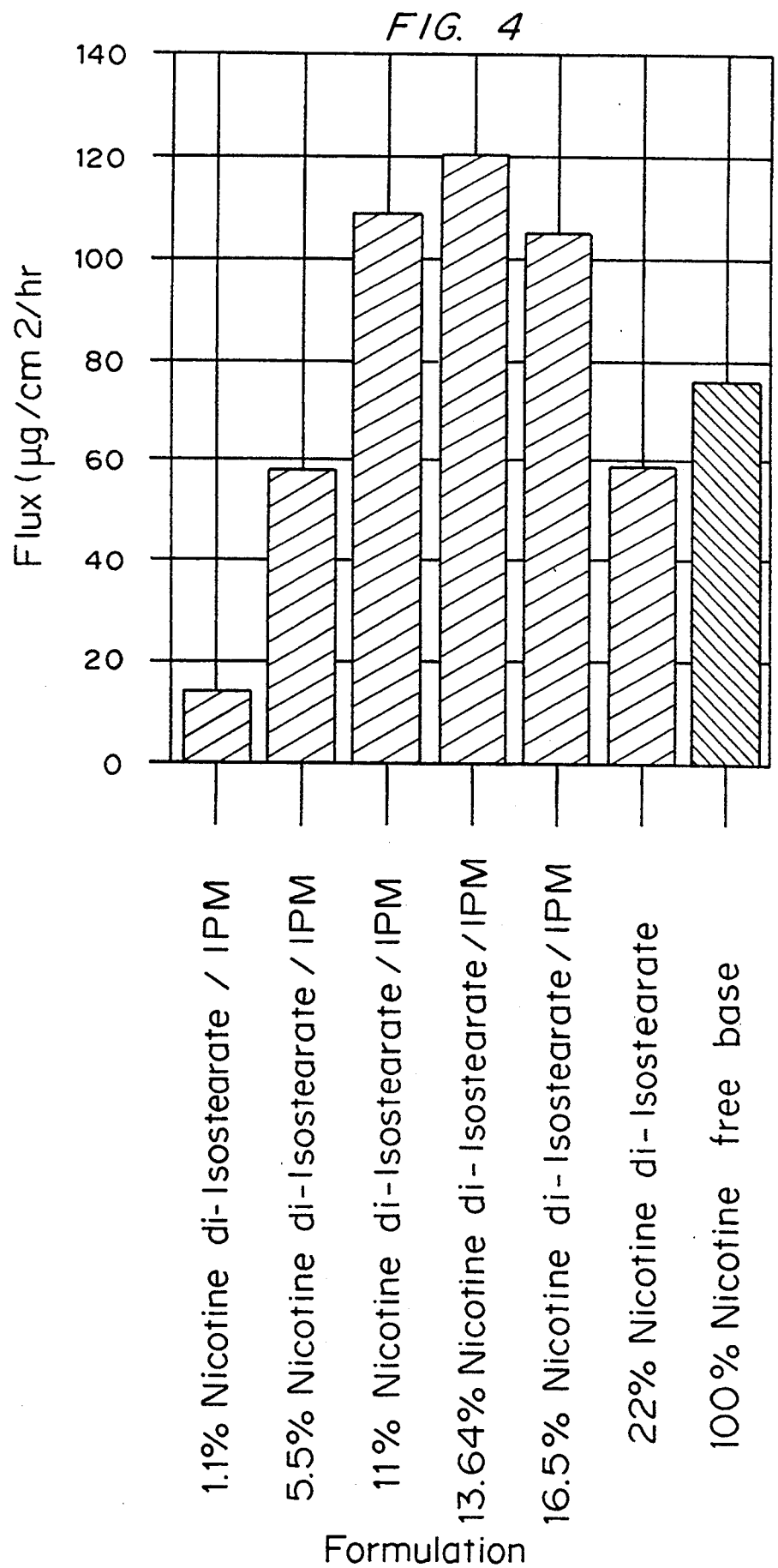

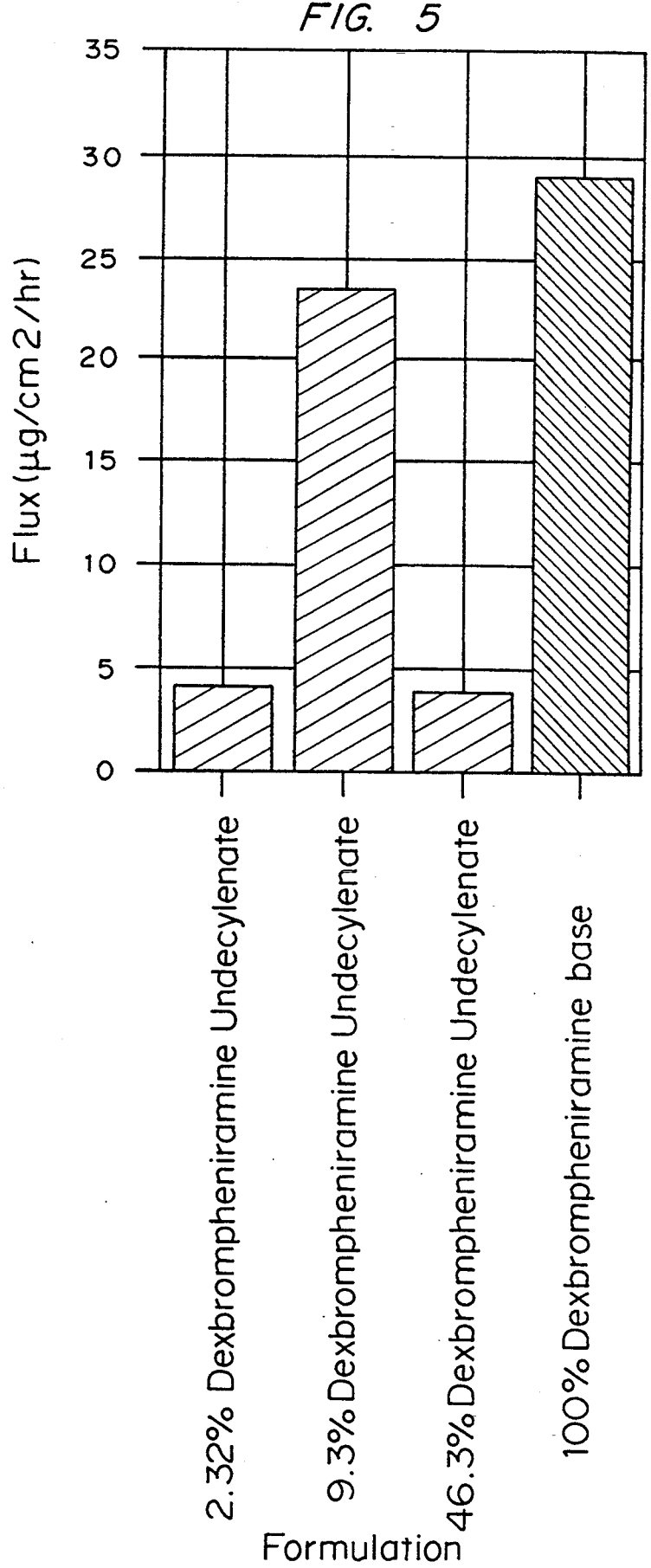

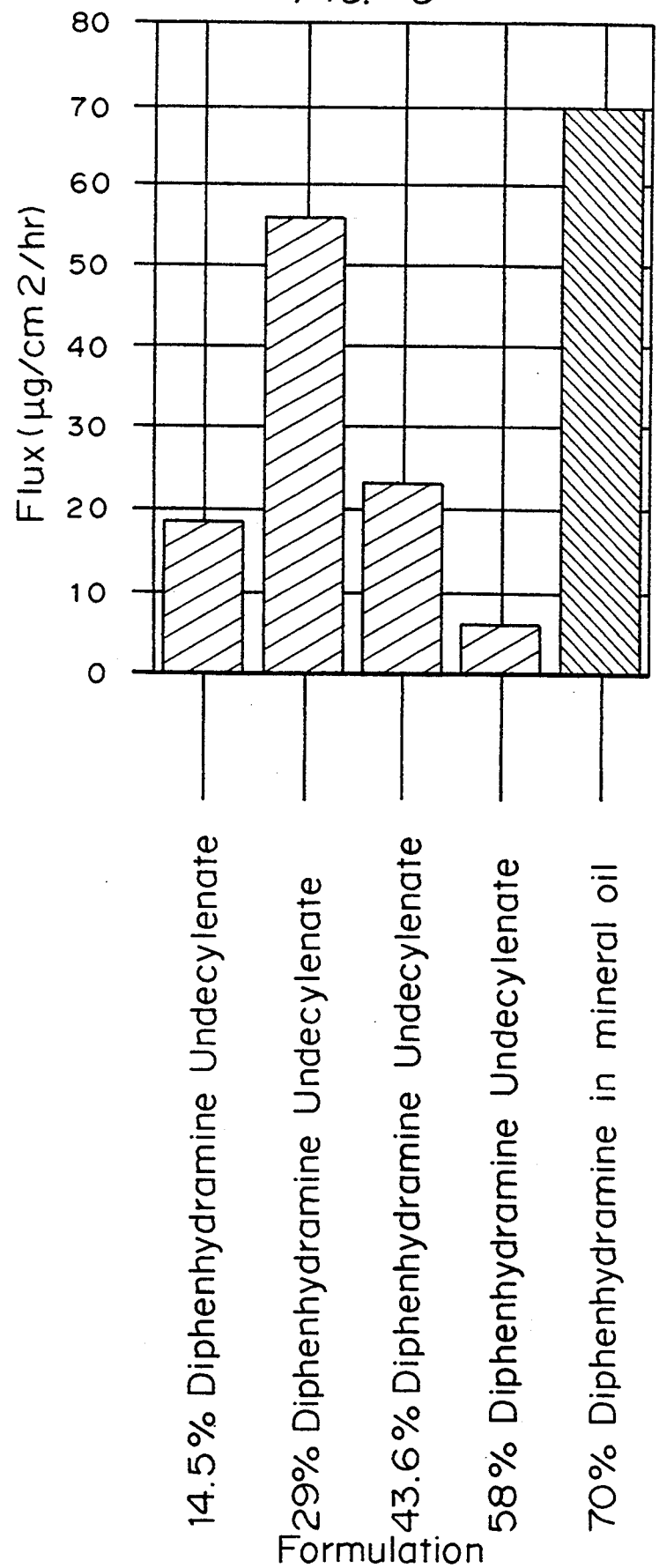

TRANSDERMAL ADMINISTRATION OF AMINES WITH MINIMAL IRRITATION AND HIGH TRANSDERMAL FLUX RATE

This application is a continuation-in-part of U.S. Ser. No. 07/296,406, filed on Jan. 9, 1989, that is a continuation of U.S. Ser. No. 06/928,922, filed on Nov. 7, 1986, both now abandoned.

This invention is in the area of the transdermal, percutaneous or local administration of physiologically active amines to humans in a manner that minimizes skin irritation while maintaining a high transdermal flux rate.

BACKGROUND OF THE INVENTION

Transdermal patches are gaining wide acceptance in the medical community as a desirable means to deliver physiologically active substances. Transdermal patches allow the patient to receive an approximately constant supply of medication over an extended period of time, without the need to dose himself. A patient will, in general, however, not tolerate a patch that is too large or that is uncomfortable or irritating to the skin. This irritation is particularly evident when physiologically active amines in the free base form such as chlorpheniramine, diphenhydramine or dexbrompheniramine are placed on the skin.

Transdermal patches must be capable of administering the required daily dose of the substance. The slower the transdermal flux rate of the active substance, the larger the patch must be to deliver the appropriate amount of substance to satisfy the dosage requirement. In general, transdermal patches should be less than 20 to 25 square centimeters, and more usually, less than 6 square centimeters. Therefore, there is an absolute lower limit in transdermal flux rate for each active substance or composition to be able to administer it in the form of a patch of reasonable size.

It is known that physiologically active amines in their nonionized form in general penetrate the skin easily and quickly (i.e., have a high transdermal flux rate). In fact, physiologically active amines in the nonionized form are generally considered to be the fastest traveling passive, transdermally diffusing compounds known (Michaels, A. S., Chandrasekaran, S. K., Shaw, J. E., Drug permeation through human skin: theory and in vitro experimental measurement. A.I.Ch.E.J., 1975, 21, 985-996.). Physiologically active free amines, however, are often very irritating when administered through the skin (i.e., transdermally), often causing blisters, erythma, pruritus, and burning. Examples of transdermal patches that exhibit these topical adverse effects include the Habitrol TM and Prostep TM transdermal systems for the systemic delivery of nicotine, which is a tertiary amine. Prior art compositions that have been formulated to reduce the irritating property of the amine free base, have done so at the expense of a significant reduction in the transdermal flux rate of the pharmaceutical composition. This significant reduction in transdermal flux rate decreases the usefulness of the composition in a transdermal patch, because of the large size of the patch needed to deliver an appropriate amount of the active substance. As an example, physiologically active amines such as chlorpheniramine can be delivered in the form of maleate ($HO_2CCH=CHCO_2H$) salts. The maleate salt of the amine is significantly less irritating than the uncomplexed physiologically active amine, as noted in Table 1 of the application. Maleate amine salts, however, travel so slowly through the skin that they are typically not useful for transdermal delivery. The same is true of water soluble salicylate salts of amines.

Physiologically active amines in the free base form have also been provided in a number of pharmaceutically acceptable carriers, including nonpolar solvents. However, the amines were either: (1) nonirritating to begin with; (2) were delivered in their irritating state; or (3) were complexed as salts that have unsuitably low flux rates for transdermal patch delivery. For example, European Patent Application No. 0 262 753 teaches a transdermal delivery system that includes a physiologically active amine, scopolamine, dissolved in a solvent such as mineral oil or isopropyl myristate. This reference does not teach how to reduce the irritation of the uncomplexed amine on delivery. French Patent Application No. 2 397 190 discloses that clonidine can be transdermally administered in a nonpolar solvent. This reference also does not address how to complex the amine to reduce irritation. British Application No. 2 140 019 discloses a drug delivery system that includes an active amine in a mineral oil. As with the other two applications, this reference does not address how to prepare a formulation that minimizes irritation.

WO 86/00806 is directed to the identification of an antihistaminic drug that is nonirritating and that has a suitably high flux rate. The inventors attacked this problem by screening the irritation and flux rate of a number of antihistaminic amines (see Table 1 of the reference). They identified one agent, azatadine, that was nonirritating and that had a suitably high flux rate. The WO 86/00806 publication, on page 7, states that "It is surprising to find that after numerous antihistamines were tested, there was only one antihistamine, azatadine, that had good dermal penetration and no dermal irritation or sensitization." This reference highlights the need for a method and composition to administer an irritating physiologically active amine in a nonirritating formulation that provides a suitably high transdermal flux rate.

U.S. Pat. No. 2,735,799 discloses a method of making an epinephrine composition that protects the epinephrine from oxidation. The patent discloses the use of the HCl, bitartrate, sulfate, and borate salts (see column 1, lines 25-28). These physiologically active amine salts are unsuitable for transdermal delivery because they are water soluble salts and would have low transdermal flux rates.

U.S. Pat. No. 3,304,230 discloses that a salt formed between a water soluble amine and a $C_4$ to $C_{18}$ monocarboxylic acid is soluble in volatile aerosol repellant fluids and still retains water solubility (see column 1, lines 58-72, and column 2, lines 26-36). The patent is not directed to compositions for controlled transdermal delivery, but instead, to volatile aerosol compositions for inhalation. The patent does not teach or suggest haw to formulate physiologically active amines in a manner that minimizes skin irritation while maintaining a high transdermal flux rate.

U.S. Pat. No. 4,690,683 to Chien, et al., discloses a transdermal varapamil delivery device that includes the active material in a bioacceptable lipophilic polymer that contains an effective amount of the active drug and an effective amount of a transport enhancing agent. The Chien reference teaches that the preferred transport enhancing agents are isopropyl myristate, n-decylmethylsulfoxide, oleyl alcohol, propyl oleate, 1- dodecylazacycloheptan-2-one, and N,N-diethyl-m-toluamide. Other transport enhancing materials listed by Chien include thioglycolate salts, fatty alcohols, saturated and unsaturated fatty acids, glycol monoesters of fatty acids, and fatty acid monoglycerides. Chien also discloses that a combination of these materials can be used, for example, isopropyl myristate (a fatty ester) and N,N-diethyl-m-toluamide (an amide). The patent teaches that to maintain the proper pH for delivery, an acid such as disodium hydrogen phosphate/citric acid can be incorporated into the adhesive. This patent does not appear to address how to minimize the irritability of the composition.

Given the convenience of transdermal patches as a means for the delivery of normally irritating physiologically active amines, and the ability of the patches to provide a constant supply of medication over an extended period of time without the need for periodic dosages, it would be of great benefit to have a method and composition that minimizes irritation without serious compromise of the transdermal flux rate.

Therefore, it is an object of the present invention to provide a method and composition for the transdermal, percutaneous or local administration of physiologically active amines to humans in a manner that minimizes skin irritation while maintaining a high transdermal flux rate.

SUMMARY OF THE INVENTION

It has been discovered that physiologically active amines can be administered transdermally or topically to humans in a manner that minimizes skin irritation while maintaining a high transdermal flux rate by the appropriate selection of: (1) a complexing agent for the physiologically active amine; (2) a solvent for the complexed amine; (3) the amount of the complexing agent used in relation to the amine; and (4) optionally, the amount of solvent used for the complexed amine. It is critical to the success of the invention that all of these factors be simultaneously considered.

Specifically, it has been discovered that physiologically active amines can be administered transdermally with low skin irritation and high flux rate by administering the amine as: a minimally or nonirritating salt of a stoichiometric molar excess of a fatty acid of from 8 to 20 or 22 carbon atoms in a nonpolar, nonvolatile solvent. In a preferred embodiment, the nonpolar, nonvolatile solvent is included in an appropriate amount such that the transdermal flux rate is at least 50%, and typically at least 70%, that of the uncomplexed, unsolvated physiologically active amine.

The amount of nonpolar, nonvolatile solvent needed to obtain a flux rate that is at least 50%, and typically at least 70%, that of the uncomplexed, unsolvated physiologically active amine, is determined by graphing the transdermal flux rate of the composition versus the amount of nonpolar, nonvolatile solvent in the composition, and comparing the plot to the transdermal flux rate of the uncomplexed, unsolvated amine, as described in detail below. It was found, surprisingly, that when the salt of the amine is administered in a nonirritating, nonvolatile, nonpolar solvent, as the amount of solvent in the composition increases, the transdermal flux rate increases to a maximum level and then typically decreases again. The top of the curve represents the optimal amount of solvent for high transdermal flux. In fact, the composition represented by the top of the curve has a transdermal flux rate that typically exceeds even that of the transdermal flux rate of the uncomplexed, unsolvated amine. This could not have been predicted on the basis of any known prior art in this area.

Using the method disclosed herein for the transdermal administration of physiologically active amines, a wide variety of active amines can be delivered in an effective and constant dosage, in a manner that has minimal adverse effect on the skin, through a transdermal patch of 25 cm$^2$ or less, and more typically, significantly less than 20 cm$^2$.

This methodology represents a significant advance in the art of transdermal delivery in that it will allow, for example, the transdermal administration of nicotine to patients attempting to stop smoking but who cannot tolerate the currently marketed nicotine patches. The method described herein can also be used to deliver an effective and constant dosage of an antihistamine such as chlorpheniramine (a primary skin irritant) to patients suffering from allergies and asthma, through a relatively small transdermal patch without significant topical adverse effects. In fact, based on an estimated flux of 90 mcg chlorpheniramine/hour needed to achieve therapeutic blood levels of the drug, a nonirritating chlorpheniramine patch using only pharmaceutically acceptable ingredients can be provided using this method that is approximately 3 cm$^2$, in area (8.5% chlorpheniramine, 11.7% undecylenic acid, and 79.9% isopropyl myristate, as illustrated in FIG. 2).

BRIEF DESCRIPTION OF THE FIGURES

FIG. 2 is a graph of the transdermal flux rate through human skin in micrograms per centimeter$^2$ per hour of compositions prepared with varying combinations of the 1:2 molar ratio salt of chlorpheniramine and undecylenic acid with isopropyl myristate as the solvent, as described in Example 8, Table 4.

FIG. 3 is a graph of the transdermal flux rate through human skin in micrograms per centimeter$^2$ per hour of compositions prepared with varying combinations of the 1:2 molar ratio salt of chlorpheniramine and undecylenic acid with isopropyl oleate as described in Example 9, Table 5.

FIG. 4 is a graph of the transdermal flux rate through human skin in micrograms per centimeter$^2$ per hour of the 1:2 molar ratio salt of nicotine and isostearic acid in isopropyl myristate, as described in Example 10, Table 6.

FIG. 5 is a graph of the transdermal flux rate through human skin in micrograms per centimeter$^2$ per hour of dexbrompheniramine and undecylenic acid (1:2 molar ratio) in varying amounts of isopropyl myristate, as described in Example 11, Table 7.

FIG. 6 is a graph of the transdermal flux rate through human skin in micrograms per centimeter$^2$ per hour of a 1:1 molar ratio of undecylenic acid to diphenhydramine in varying amounts of isopropyl myristate, as described in Example 12, Table 8.

DETAILED DESCRIPTION OF THE INVENTION

Figure 1:
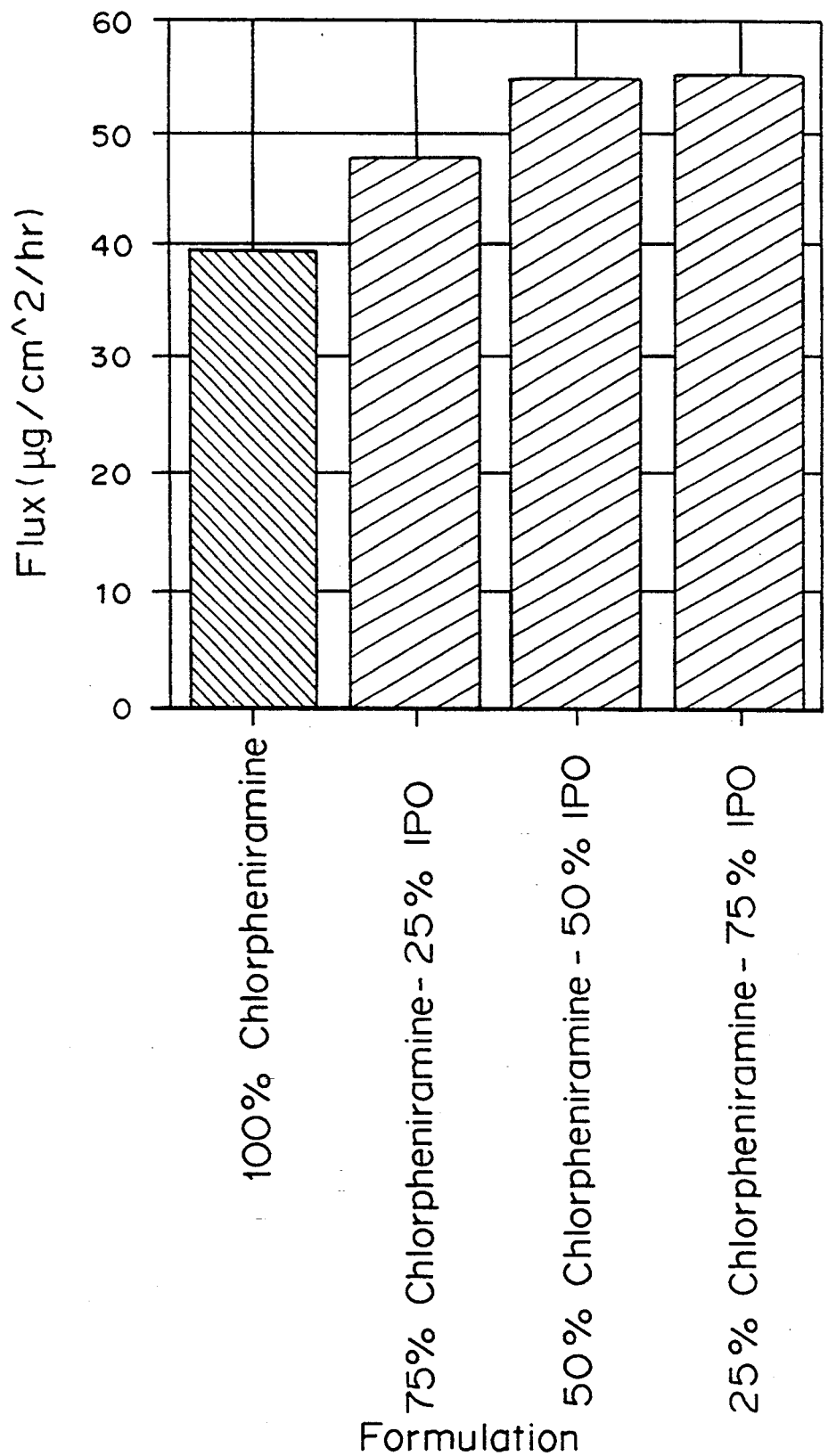
FIG. 1 is a graph of the transdermal flux rate through human skin in micrograms per centimeter$^2$ per hour of 100% chlorpheniramine, 75% chlorpheniramine/25% isopropyl oleate (wt/wt), 50% chlorpheniramine/50% isopropyl oleate, and 25% chlorpheniramine/75% isopropyl oleate, as described in Example 7, Table 3.

It has now been discovered that an effective amount of a skin irritating physiologically active amine can be transdermally or topically administered in a minimally or nonirritating composition that maintains a suitably high transdermal flux rate, by providing the amine as a minimally or nonirritating salt of a stoichiometric molar excess of a fatty acid of from 8 to 20 or 22 carbon atoms, in a nonpolar, nonvolatile solvent. In a preferred embodiment, the nonpolar, nonvolatile solvent is included in an appropriate amount such that the transdermal flux rate is at least 50% by weight, and typically at least 70%, that of the uncomplexed, unsolvated physiologically active amine.

The term skin irritating physiologically active amine, as used herein, refers to a physiologically active amine that obtains an irritation rating of greater than 3 in Procedure A, set out below, or a score of 2 or greater in Procedures B or C, also set out below.

In an alternative embodiment, a method is provided for the improved delivery of physiologically active amines that cause only slight erythema (which obtain a score of 3 or less in Procedure A, set out below or a score of less than 2 in Procedures B or C), whereby the amine is provided in a composition that exhibits less irritation (typically decreasing the irritation rating by half, and more typically by at least 70 or 80 percent), while providing a transdermal flux rate that is at least equal to that of the uncomplexed physiologically active amine.

I. Experimental Procedures for the Measurement of Irritation

Irritation can be measured through a wide variety of techniques known to those of ordinary skill in the art. Any of these methods can be used to evaluate the compositions described herein. Examples of three methods for measuring irritation, as well as the scaling system used to evaluate the results, are set out in detail below. It will be noted that a different scoring system was used for Procedure A (a seven point scale) than that for Procedures B and C (a five point scale). The results of evaluations throughout the text can be normalized as by standard calculation. All percentages are by weight unless otherwise indicated.

Procedure A Primary Irritation Study in Humans
The test compound was evaluated for skin irritancy by absorbing the material in a porous cellulose triacetate film (0.02 inch thick) prepared as described in U.S. Pat. No. 3,846,404 (MA-92 POROPLASTIC film). Patches of the saturated film 2 cm² in area were placed by test subjects on their own forearm skin and held in place by clear, nonocclusive adhesive (Tegaderm), allowing constant observation of the skin under the patch. After 17 hours, skin damage was evaluated by visual observation. The damage was ranked using the following scale: 1 (no discoloration, no erythema); 2 (pink coloration, slight erythema); 3 (reddening, moderate erythema, no burning); 4 (reddening and burning, moderate erythema); 5 (erythema and edema, with or without burning); 6 (severe erythema, edema, and burning); and 7 (severe erythema, severe burning, blistering, and edema).

Procedure B Primary Irritation Study in Human-Alternative Method Finn Chambers (Epitest, Ltd OY, Tuusula, Finland) for epicutaneous testing of irritation on Scanpor adhesive (Nörgesplaster A/S, Norway; 10 chambers) were used to test the primary irritancy of the test compound or composition. The formulations were introduced into the Finn Chambers using the following procedures. The adhesive covering was removed and the filter paper dots were placed into the chambers to be used. A disposable pasteur pipette was used to add one drop of formulation onto the filter paper. The pipette was then discarded. This was repeated for each formulation, up to 10 formulations. The subjects' forearm was lowered onto the scanpor adhesive and pressure was applied to insure adhesion. Two strips of 2" paper tape were overlapped over the scanpor adhesive. This remained in place for 24 hours, at which time it was removed and scored immediately using the table below.

| ERYTHEMA AND ESCHAR FORMATION | Score |
|---|---|
| No erythema | 0 |
| Very slight erythema (barely perceptible) | 1 |
| Well defined erythema | 2 |
| Moderate to servere erythema | 3 |
| Severe erythema (beet readness) to slight eschar formation (injuries in depth) | 4 |

Procedure C Primary Skin Irritation Tests in Animals
Tests were performed on young adult albino rabbits (New Zealand White rabbits). Six rabbits were used for each test. The rabbits were prepared for the test by clipping the hair from the backs of the rabbits and any rabbit showing skin damage from the clipping was rejected from the testing. The application sites for the transdermal drug delivery (TDD) patch was intact skin. As an example, a formulation containing the test composition was incorporated into Poroplastic ® transdermal patches. One TDD patch containing the test material was applied to one side of the rabbit's back. The size of the patch did not to exceed one (1) inch in diameter or one (1) inch square. A one (1) inch square gauze patch, two single layers thick, was used to cover the test TDD patch. The animals were immobilized with patches secured in place by adhesive tape. The entire trunk of the animal was then wrapped with an impervious material for the twenty-four (24) hour exposure period. After 24 hours of exposure the patches were removed and the resulting reactions evaluated on the basis of the scoring system indicated below. Observations were again made at the end of a total of 72 hours (48 hours after the first reading). A primary irritation score was obtained by adding the values for erythema and eschar formation at twenty-four and seventy-two hours to the values for edema formation at twenty-four and seventy-two hours. The total of the values was divided by two to give the irritation score.

| | Score |
|---|---|
| ERYTHEMA AND ESCHAR FORMATION | |
| No erythema | 0 |
| Very slight erythema (barely perceptible) | 1 |
| Well defined erythema | 2 |
| Moderate to servere erythema | 3 |
| Severe erythema (beet readness) to slight eschar formation (injuries in depth) | 4 |
| EDEMA FORMATION | |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond area of exposure) | 4 |

II. Experimental Procedure for the Measurement of Transdermal Flux Rate

A surgically-removed human skin source was used for all in vitro diffusion cell tests. Skin was obtained from 37 (plus or minus 13) year-old healthy females undergoing reduction mammaplasty operations. The epidermis-stratum corneum layer was separated from full-thickness skin using published techniques (Blank, I. H.; Griesemer, R. D.; Gould, E. J. *Invest. Dermatol.* 1957, 29, 299–309.). Briefly, the full-thickness skin was immersed in distilled water heated to 60±1 degrees C for 45 seconds. The epidermal-stratum corneum layers were then peeled from the dermis. The epidermis-stratum corneum layers were then excised with a cork borer into circular disks 1.4 cm in diameter.

The skin was then mounted onto a Teflon flow-through diffusion cell. The diffusion cell was described by Brown et al (Brown, LR, Cline, JF, Raleigh, CL and Henry, MB in Controlled Release Technology, Pharmaceutical Applications, American Chemical Society Symposium Series #348, Lee, PI, and Good WR eds, American Chemical Society, Washington, DC, 1987 pp 113–119.). The skin sample of the donor portion of the diffusion cell was secured in place into the receptor cell. The flow-through cell consisted of a Teflon receptor cell with an exposed skin surface area of 0.32 $cm^2$ and a receptor cell volume of 0.13 mi. Sink conditions were maintained by pumping phosphate-buffered saline under the skin in the receptor cell at about 3 ml/hr. Thus, the receptor volume was replaced about 23 times per hour. These cells were then mounted on a water-jacketed bracket which maintained the receptor solution in the cells at 33 degrees C. The receptor media which was pumped under the cells was degassed in order to reduce air bubble formation under the skin. Bubble traps at the inlet of the cells were also added to trap bubbles before they could become caught under the skin.

Continuous automatic sampling was carried out from these cells into ordinary liquid scintillation vials by an ISCO brand (Lincoln, N. E.) Retriever III fraction collector whose timing mechanism was been altered so that nine timepoints could be sampled in intervals of up to 99.0 hours for 14 diffusion cells.

The radiolabeled form of the pharmaceuticals under investigation was used to assay the quality of drug which has diffused through the skin. The radiolabeled assay was confirmed by additionally analyzing the drug by HPLC. Liquid scintillation fluor was added directly to the sample vials so that they could be measured with minimal liquid transfers and handling. The sample vials were then analyzed with appropriate quench correction techniques by liquid scintillation spectroscopy.

The resulting data was plotted as cumulative $\mu g$ of drug diffused versus time. The slope after the initial lag time was used to calculate the flux rate of each formulation. Each formulation was tested in at least triplicate samples.

III. Selection of Physiologically Active Amine to be Administered

A physiologically active amine in the free base form can be evaluated for skin irritancy by Procedures A, B, or C, set out above. Alternatively, irritation can be determined by other conventional patch test involving maintaining the amine in contact with the skin for 24 hours, and then observing the skin. The results are evaluated using the scales provided for Procedures A, B, or C as defined herein.

Any irritating physiologically active amine (i.e, that obtains an irritation rating of greater than 3 in Procedure A, or a score of 2 or greater in Procedures B or C) can be transdermally delivered in a minimally irritating manner with high transdermal flux rate using the method disclosed herein. In the alternative embodiment, a physiologically active amine that is only slightly irritating (which obtain a score of 3 or less in Procedure A, set out below or a score of less than 2 in Procedures B or C), can be provided in a composition that has even less irritation (typically decreasing the irritation rating by half, and more typically by at least 70 or 80 percent), while providing a transdermal flux rate that is at least equal to that of the uncomplexed, physiologically active amine.

Nonlimiting examples of suitable amines include nicotine, chlorpheniramine, diphenhydramine, bromodiphenhydramine, doxylamine, phenyltoloxamine, carbinoxamine, methapheniline, pyrilamine, tripelennamine, methapyrilene, chlorothen, thenyldiamine, methafurylene, thonzylamine, pheniramine, brompheniramine, dexchlorpheniramine, dexbrompheniramine, pyrrobutamine, promethazine, pyrathiazine, trimeprazine, methdilazine, isothipendil, ephedrine, epinephrine, norepinephrine, isoproterenol, phenylephrine, butanefrin, amphetamine, vonedrine, cyclizine, clorcyclizine, scapolamine, clonidine, nifedipine, diphenylpyraline, phenindamine, dimethypyrindene, clemizole, arecoline, pilocarpine, lidocaine, procaine, hydroxyzine, and the like.

The clearance and the effective blood level needed to achieve therapeutic blood levels for each of these physiologically active amines can be obtained by reference to a standard text used by those in the industry, such as Goodman & Gilman, The Pharmacological Basis of Therapeutics, A. G. Goodman, T. W. Rall, A. S. Nies, P. Taylor, Editors, Pergamon Press $8^{th}$ Edition, New York 1990. Given this information and the empirically determined transdermal flux rate of the material, the required patch size in $centimeters^2$ for effective dosing can be determined. The dosing rate in micrograms per hour needed to achieve therapeutic blood levels of the physiologically active amines is calculated by multiplying the clearance of the drug through the blood, times the effective blood level needed for treatment. The calculated therapeutically effective dosing rate is then converted to micrograms per hour by standard calculation. The estimated patch size is determined by dividing the calculated therapeutically effective dose rate by the in vitro transdermal flux rate.

IV. Selection of Complexing Agent

The epidermal skin layer provides the physical barrier to drug penetration. The epidermis contains the stratum corneum layer of dead keratinized cells. Free fatty acid and ceramide molecules separate these dead keratinized cells from each other and allow the diffusion of fat soluble molecules through these lipids (Elias, P. M. Epidermal lipids, barrier function and desquamation. J. Invest. Dermatol. 80: 44–49.). Water soluble molecules cannot partition into and diffuse through the stratum corneum effectively. The aqueous environment of the remainder of the epidermal skin layer prevents the partitioning and diffusing of very lipophilic molecules through the epidermal layer. Those drug molecules which have the greatest possibility of diffusing through the skin, therefore, are those which have appreciable lipid and water solubilities. For example, the uncomplexed physiologically active amine permeates the skin much more readily than its more water-soluble ionized form (Michaels, A. S., Chandrasekaran, S. K., Shaw, J. E., Drug permeation through human skin: theory and in vitro experimental measurement. A.I.Ch.E.J., 1975, 21, 985–996.).

A practical consequence of the structure of the stratum corneum layer of the skin is that the water soluble salt forms of amine drugs such as chlorpheniramine maleate, brompheniramine maleate, chlorpheniramine tannate, and diphenhydramine hydrochloride, while minimally irritating, do not permeate the skin with a therapeutically effective flux rate. This is because these drug forms cannot dissolve in or partition effectively into the lipophilic structures of the stratum corneum.

The largest transdermal flux rate observed by the Applicants for the nonirritating, water soluble, chlorpheniramine maleate salt is 5.02 micrograms/cm$^2$/hr at saturation concentration. The estimated patch size for such a composition can be calculated as described in detail above. Using this calculation, it is estimated that the water soluble salt formulation would require a transdermal patch area greater than 39 cm$^2$. This is larger than the desirable upper limit of 25 cm$^2$ patch area for patient acceptability. Since water soluble salt forms of physiologically active amines are not at all soluble in nonpolar, nonvolatile solvents, these solvents cannot be used to increase their transdermal flux rate.

It has been discovered that a complex formed by the combination of a stoichiometric molar excess of a fatty acid of from 8 to 20 or 22 carbon atoms with a physiologically active amine in a composition with a nonpolar, nonvolatile solvent is capable of diffusing through the stratum corneum layer of the epidermis. The term fatty acid, as used herein, includes straight and branched chain compounds. Mixtures of fatty acids can also be used.

It has also been discovered that unsaturated fatty acids tend to decrease the skin irritation of certain physiologically active amines more significantly than saturated fatty acids. The trend appears to be that the more irritating the amine, the more significant the difference in irritation between the unsaturated fatty acid amine salt and the saturated fatty acid amine salt. For example, chlorpheniramine in the free base form is a severe skin irritant that has an irritation rating of 7 using Procedure A. Table 1 below provides the irritation ratings obtained using Procedure A for a number of saturated and unsaturated fatty acid salts of chlorpheniramine. For comparative purposes, Table 1 also provides the irritation rating for chlorpheniramine maleate and chlorpheniramine salicylate (that as explained above, have unsuitably low transdermal flux rates). As indicated in Table 1, when one mole of chlorpheniramine is complexed with two moles of a saturated fatty acid such as stearic acid, myristic acid, or isostearic acid, the irritation rating ranges from 3 to 4. However, when 1 mole of chlorpheniramine is complexed with 2 moles of an unsaturated fatty acid such as oleic acid, undecylenic acid, or octenoic acid, the irritation rating ranges from 1.5–2.3. Therefore, in one embodiment, the invention includes administration of a normally irritating physiologically active amine that in the absence of a fatty acid would have an irritation rating of 5, 6, or 7, wherein the amine is combined with an unsaturated fatty acid of from C8–22.

TABLE I

| Formulation | | Number of Skin Tests | Irritation Rating (1–7) |
|---|---|---|---|
| 1. FREE BASE | | | |
| a. | Chlorpheniramine Base | 2 | 7.0 |
| b. | Chlorpheniramine Base, 23.5% solution in isopropyl oleate (IPO) | 2 | 6.5 |
| 2. SATURATED FATTY ACID SALTS | | | |
| a. | Chlorpheniramine Stearate (1:2 M) | 4 | 4.0 |
| b. | Chlorpheniramine Myristate (1:2 M) | 2 | 3.0 |
| c. | Chlorpheniramine Isostearate (1:2 M) | 1 | 3.5 |
| 3. UNSATURATED FATTY ACID SALTS | | | |
| a. | Chlorpheniramine Oleate (1.3 M) | 2 | 1.0 |
| b. | Chlorpheniramine Oleate (1.:2 M) | 21 | 2.3 |
| c. | Chlorpheniramine Oleate (1:1 M) | 26 | 3.5 |
| d. | Chlorpheniramine Undecylenate (1.3 M) | 2 | 1.0 |
| e. | Chlorpheniramine Undecylenate (1.2 M) | 2 | 2.0 |
| f. | Chlorpheniramine Undecylenate (1.:2 M) in 70% IPO | 14 | 1.4 |
| g. | Chlorpheniramine Octenoate (1.2 M) | 2 | 1.5 |
| h. | Chlopheniramine Linoleate (1:1 M) | 1 | 3.0 |
| 4. CARBOXYLIC ACID SALTS | | | |
| a. | Chlorpheniramine Maleate (1:1 M) | 9 | 1.0 |
| b. | Chlorpheniramine Salicylate (1:1 M) | 2 | 1.0 |

In another embodiment of the invention, a less irritating amine, such as hydroxyzine that has an irritation of 2 or less using Procedure B, or nicotine, that has an irritation rating of less than 2 when using Procedure C is administered transdermally through the skin as a complex of either a saturated or unsaturated fatty acid. For example, some saturated fatty acids, including isostearic acid, appear to effectively reduce the irritation rating of nicotine.

One mole of hydroxyzine combined with 1, 2, or 3 moles of undecylenic acid (an unsaturated acid) has an irritation rating of 0.2 using Procedure B. One mole of the same amine in combination with 1, 2, or 3 moles of oleic acid also has an irritation rating of 0.2 using the same procedure.

Any straight or branched chain fatty acid that falls with the formula of a fatty acid of from 8 to 20 or 22 carbon atoms can be used in the method and composition disclosed herein. Aliphatic, unsaturated fatty acids are selected so that they form a lipophilic, oily liquid when combined with the free amine. Nonlimiting examples include but are not limited to undecylenic, oleic, octenoic, linoleic, palmitoleic acid, oleic acid, linoleic acid, linolenic acid, arachidonic acid, cetoleic acid, erucic acid, docosahexanoic, elaidic, nervonic, and petriselinic acids and the like.

Saturated fatty acids include but are not limited to lauric, myristic, stearic, isostearic, caproic, caprylic, capric, palmitic, arachidic, behenic, lignoceric, heptanoic, nonanoic, undecanoic, tridecanoic, pentadecanoic, heptadecanoic, nonadecanoic, heneicosanoic, and tricosanoic acids.

V. Amount of Complexing Agent used in Relation to the Amine

It has been discovered that the molar ratio of complexing agent used in relation to the molar ratio of physiologically active amine in the free base form can be critical to the minimization of the irritation of the resulting composition. Again, it has been observed that the molar ratio of complexing agent (the fatty acid) to nonionized amine has a more significant effect on the irritation rating of physiologically active amines that alone have an irritation rating of 4, 5 or greater (using Procedure A), than on less irritating amines. Therefore, in one embodiment, the invention is a method and composition for the delivery of irritating physiologically amines that includes administering the amine in combination with greater than one mole of the complexing agent (a stoichiometric molar excess).

Referring to Table 1, a 1:1 chlorpheniramine oleate salt exhibits an irritation rating of 3.5 using Procedure A. The 1:2 salt of chlorpheniramine and oleic acid exhibits a 2.3 irritation, and the 1:3 salt a skin irritation of 1.0. Likewise, a 1:2 chlorpheniramine undecylenate salt exhibits an irritation rating of 2.0 using Procedure A, and the 1:3 salt of chlorpheniramine and undecylenic acid a skin irritation of 1.0. However, 1 mole of hydroxyzine (a minimally irritating amine) combined with 1, 2, or 3 moles of undecylenic acid (a saturated acid) has an irritation rating of 0.2 using Procedure B. One mole of the same amine in combination with 1, 2, or 3 moles of oleic acid also has an irritation rating of 0.2 using the same procedure.

VI. Selection of Nonpolar, Nonvolatile Solvent

Complexation of the physiologically active amine with one or a mixture of the above-described fatty acids in the proper stoichiometric amount significantly reduces the skin irritation of the amine, yet also reduces the transdermal flux rate of the amine. It was discovered that the transdermal flux rate of the amine can be restored, in part or whole, while maintaining amine is in the less irritating fatty acid salt form, in such a manner that allows for controlled delivery in a patch of 25 cm$^2$ or less, and often below 10 or 20 cm$^2$, by formulating the fatty acid amine complex in a nonpolar, nonvolatile solvent.

The term nonpolar, nonvolatile solvent as used herein refers to a pharmaceutically acceptable liquid that is nontoxic, nonirritating and lipophilic. The solvent must be chemically inert to the amine salt. Useful solvents typically have a dielectric constant of less than 4 and a boiling point above 150° C. More volatile solvents are undesirable because of they tend to evaporate while in contact with the skin, leaving an unsolvated amine fatty acid salt complex that has an unacceptably low transdermal flux rate.

The transdermal flux rate of the composition, as well as the optimal amount of solvent to be used, will vary depending on the solvent selected. Given the disclosure herein, including the working examples below, one of ordinary skill in the art will be able to select the optimal solvent and optimal weight ratio of solvent for the desired application.

The solvent must be selected such that the rate of transport of the fatty acid salt through the skin is sufficiently high that a pharmaceutically effective concentration of the drug can be achieved with a skin contact area of reasonable size. In general, the maximum area of skin contact that is practical for a single application should be no greater than 20 or 25 cm$^2$, and preferably less than 6 cm$^2$. In a modification of the invention, two or more skin application sites can be used simultaneously on separate skin areas.

Fatty esters that can be used as solvents for the compositions include the esters of any of the above-defined fatty acids that have been esterified with linear, branched, or cyclic alkyl or alkenyl groups of from $C_{1-20}$. Hydrocarbons that are used as creams or lotions can also be used, including but not limited to mineral oil and petrolatum.

Nonlimiting examples of suitable solvents include mineral oil, and fatty esters including but not limited to isopropyl myristate, isopropyl oleate, mineral oil, propyl oleate, butyl stearate, methyl stearate, isocetyl stearate, butyl acetate, butyl myristate, cetearyl octanoate, cetyl palmitate, cetyl stearate, decyl oleate, diisopropyl adipate, dioctyl adipate, glyceryl oleate, isobutyl stearate, tributyl stearate, isocetyl stearate, isodecyl oleate, isopropyl isostearate, isopropyl lanolate, isopropyl linoleate, isopropyl stearate, myristyl lactate, myristyl myristate, myristyl stearate, octyl palmitate, octyl stearate, retinyl palmitate, isostearyl myristate, diethyl maleate, ethyl laurate, glyceridacid, n-heptyl acetate, n-octyl acetate, 1-nonyl acetate, ethyl oleate, tributyl citrate, and isopropyl palmitate.

The unsaturated bond in the fatty ester can be located at any desirable location in the molecule. Examples of variations of unsaturated fatty esters include citronellyl isobutyrate, methyl undecylenate, 9-decenyl acetate, ethyl crotonate, etc. The number of unsaturated carbon atoms can be increased to include di- or polyunsaturated compounds, including fatty esters such as linalyl butyrate, neryl acetate, citronenellyl crotonate, etc. The penetration enhancing effects may vary with the degree of lipophilicity, the aliphatic chain length and the degree of unsaturation of the fatty ester. Mixtures of these solvents can also be used.

Nonpolar, nonvolatile alcohols can also be used in this method and composition, including benzyl alcohol and fatty alcohols such as dodecyl alcohol, stearyl alcohol, oleyl alcohol, ocacosyl alcohol, isopentyl alcohol, isooctyl alcohol, crotonyl alcohol, decyl alcohol, octyl alcohol, undecanol, and the like.

VII. Amount of Solvent Used for the Complexed Amine.

It was found, surprisingly, that when the salt of the amine is administered in a nonirritating, nonvolatile, nonpolar solvent, as the amount of solvent in the composition increases, the transdermal flux rate increases to a maximum level and then typically decreases again. The top of the curve represents the optimal amount of solvent for high transdermal flux. In fact, the composition represented by the top of the curve has a transdermal flux rate that typically exceeds even that of the transdermal flux rate of the free amine. This could not have been predicted on the basis of any known prior art in this area.

The exact shape of the curve, and the location of the top of the curve varies depending on the selection of physiologically active amine, the fatty acid used for complexation, the ratio of amine to fatty acid salt, the amount of nonpolar, nonvolatile solvent, and the ratio of solvent to amine salt in the composition. The amount of nonpolar, nonvolatile solvent needed to obtain a flux rate that is at least 50%, and typically at least 70, 80, or 90% that of the uncomplexed, unsolvated physiologically active amine, is determined by graphing the transdermal flux rate of the composition versus the amount of nonpolar, nonvolatile solvent in the composition, and comparing the plot to the transdermal flux rate of the uncomplexed, unsolvated amine. The top of the curve represents the optimal amount of solvent for high transdermal flux. In fact, the composition represented by the top of the curve often has a transdermal flux rate that exceeds even that of the transdermal flux rate of the free amine.

For certain compositions, satisfactory flux rates are obtained with 10 or 20 to 80 or 90 percent by weight solvent. For certain compositions, satisfactory flux rates are obtained with 40 to 60% solvent by weight in the composition.

Overall rate of transport of the amine through the skin or topically, as desired, can be adjusted by increasing the patch size, or by increasing or decreasing the area of skin with which the solution is in contact, or by varying the type and amount of fatty acid used and/or solvent used. The dosage can be adjusted by varying the amount of amine salt in the composition.

Given the disclosure herein, one of ordinary skill in the art will know how to administer a wide variety of physiologically active amines transdermally or locally to humans in a manner that minimizes skin irritation while maintaining a high transdermal flux rate. All of these variations are considered within the scope of the invention. The invention is further described below through detailed working examples. The examples are merely illustrative, and are not intended to limit the scope of the method or compositions of the invention. A number of the following examples are intended to illustrate typical skin penetrating formulations with variations in fatty composition and drug composition. All materials used in these compositions are available as USP grade components that are included in the Cosmetic, Toiletry, and Fragrance Ass., Inc., International Cosmetic Ingredient Dictionary, Nikitakis, et al., Washington, D.C. 1991. The materials described in these examples are generally considered safe for topical application, and are often employed in topically-applied perfumes, cosmetics, or used as flavoring agents in food additives.

For certain compositions, satisfactory results are obtained that contain approximately 10 or 20% to 80 or 90% by weight of solvent based on the total weight of solvent and amine salt. For certain compositions, appropriate results are obtained at 40 to 60% by weight solvent composition.

Example 1 Preparation of 1:2 Chlorpheniramine Undecylenate Salt in Isopropyl

| Ingredient | Percent (by weight) |
|---|---|
| a. chlorpheniramine | 13 |
| b. undecylenic acid | 17 |

-continued

| Ingredient | Percent (by weight) |
|---|---|
| c. isopropyl oleate | 70 |

Ingredients "a" and "b" are blended mechanically to form a chlorpheniramine undecylenic acid salt that includes a one molar excess of undecylenic acid. The fatty ester isopropyl oleate is then added and mechanically blended. This formulation provides a diffusion rate through human stratum corneum which exceeds the rate of chlorpheniramine undecylenate alone, or the chlorpheniramine free base, in vitro.

Example 2 Preparation of Chlorpheniramine Undecylenate Salt in Isopropyl Oleate

| Ingredient | Percent (by weight) |
|---|---|
| a. chlorpheniramine | 11.6 |
| b. undecylenic acid | 10.3 |
| c. isopropyl myristate | 78.1 |

Ingredients "a" and "b" are blended mechanically to form the salt of chlorpheniramine with a stoichiometric excess of undecylenic acid. The solvent, isopropyl myristate is then added to provide the composition.

Example 3 Comparison of Patch Size Needed for Administration of Effective Dosage of Physiologically Active Amines The transdermal patch sizes required to deliver an effective dosage of a selected group of physiologically active amines were evaluated as described above. The results are provided in Table 2 below. As indicated, an uncomplexed solution of varapamil in isopropyl myristate prepared as described in Example 11 of U.S. Pat. No. 4,690,683 to Chien (VP23, 12.6% varapamil and 12.6% isopropyl myristate, exhibiting a flux rate of 112.38 micrograms/centimeter$^2$/hour) would require a patch size of 67.3 centimeters$^2$, which would not be tolerated by a patient. A composition of varapamil in N,N-diethyl-m-toluamide (DEET) as described in Example 12 of the '683 patent (VPS47), which provides the highest flux rate of any varapamil composition described in the examples of Chien patent, would require a patch size of 26.6 centimeters$^2$ to administer an effective dosage of drug. DEET, however, is not an appropriate solvent for extended transdermal drug delivery because it is not a United States Pharmacopeia accepted ingredient. It should also be noted that the Physician's Desk Reference indicates that the oral form of Varapamil can exhibit the following adverse skin reactions: arthralgia and rash, exanthema, hair loss, hyperkeratosis, macules, StevenJohnsons syndrome, and erythema multiforme. Chien does not teach how to minimize any of these topical effects.

In contrast, as noted in the Table, the patch sizes required for the compositions disclosed herein are typically 25 centimeters$^2$ or less, and they impart minimal irritation to the skin.

TABLE 2

| DRUG | patch size (CM2) | cal dose rate (μg/hr) | effective blood concentration (ng/ml) | Clearance (ml/min) | Transdermal flux rate (μg/cm2/hr) | source of transderm data |
|---|---|---|---|---|---|---|
| verapamil | 26.6 | 7560 | 120 | 8400 | 284 | Ex. 12 |

TABLE 2-continued

| DRUG | patch size (CM2) | cal dose rate (μg/hr) | effective blood concentration (ng/ml) | Clearance (ml/min) | Transdermal flux rate (μg/cm2/hr) | source of transderm data |
|---|---|---|---|---|---|---|
| | | | | | | VP547 Chen |
| chlorpheniramine | 3.7 | 196 | 10.6 | 308 | 53.6 | |
| dexbrompheniramine | 4.2 | 98 | 5.3 | 308 | 23.4 | |
| diphenhydramine | 11.7 | 651 | 25 | 434 | 55.8 | |
| nicotine | 7.8 | 936 | 13 | 1200 | 120 | |
| varapamil | 67.3 | 7560 | 120 | 8400 | 112 | Ex. 11 VP523 Chen |
| Chlorpheniramine maleate in water | 39.0 | 196 | 10.6 | 308 | 5.02 | |

Example 4 Evaluation of Irritation of 1:2 Chlorpheniramine Undecylenic Acid in Isopropyl Myristate A formulation containing 8.5% by weight chlorpheniramine, 11.7% by weight undecylenic acid (1 to 2 molar ratio of chlorpheniramine to undecylenic acid) and 79.7% by weight isopropyl myristate was incorporated into Poroplastic ® transdermal patches using Procedure C. One transdermal delivery device (TDD) containing chlorpheniramine was applied to one side of the rabbit's back. The size of the patch did not exceed one (1) inch in diameter or one (1) inch square. A one (1) inch square gauze patch, two single layers thick, was used to cover the test TDD. The animals were immobilized with patches secured in place by adhesive tape. The entire trunk of the animal was then wrapped with an impervious material for the twenty-four (24) hour exposure period.

After 24 hours of exposure the patches were removed and the resulting reactions evaluated on the basis of scores as described above. The primary irritation score for this chlorpheniramine formulation is 1.1 by Procedure C. The primary irritation score for uncomplexed, unsolvated chlorpheniramine is 7.0 by Procedure A.

Example 5 Evaluation of Irritation of 1:2 Nicotine Undecylenic Acid in Isopropyl Myristate Example 4 was repeated with nicotine substituted for chlorpheniramine. The primary irritation score for this nicotine undecylenate formulation was 0.

Example 6 Irritation to Human Skin of Physiologically Active Amines

Procedure B was used to evaluate the irritancy of physiologically active amines with or without complexation or solvation as described in more detail below.

a) Uncomplexed, Unsolvated Chlorpheniramine base

| Formulation | 100% (wt/wt) uncomplexed chlorpheniramine |
|---|---|
| Erythema Rating | 4.0 | b) Uncomplexed Chlorpheniramine in Various Fatty Esters

| Formulation | 30% (wt/wt) chlorpheniramine in Isopropyl oleate | 30% (wt/wt) chlorpheniramine in Isopropyl myristate | 30% (wt/wt) chlorpheniramine in Isopropyl palmitate |
|---|---|---|---|
| Erythema Rating | 3.7 | 3.6 | 3.3 |

Uncomplexed chlorpheniramine dissolved in isopropyl palmitate, myristate and oleate is a severe erythema causing agent.

c) Uncomplexed Diphenhydramine in Isopropyl Myristate or Mineral Oil.

| Formulation | 30% (wt/wt) diphenhydramine in Isopropyl myristate | 30% (wt/wt) diphenhydramine in mineral oil |
|---|---|---|
| Erythema Rating | 3.5 | 3.6 |

Uncomplexed diphenhydramine dissolved in isopropyl myristate or mineral oil is a severe erythema causing formulation.

d) Uncomplexed Hydroxyzine in Isopropyl Myristate or Isopropyl Palmitate.

| Formulation | 30% (wt/wt) hydroxyzine in Isopropyl myristate | 30% (wt/wt) hydroxyzine in isopropyl palmitate |
|---|---|---|
| Erythema Rating | 1.7 | 1.7 |

Uncomplexed hydroxyzine dissolved in isopropyl myristate or isopropyl palmitate is less irritating than chlorpheniramine or diphenhydramine. However, it does cause significant slight to well defined erythema.

e) Chlorpheniramine Complexed with Various Saturated Fatty Acids.

| Formulation | chlorpheniramine stearate (1:2 molar ratio) | chlorpheniramine myristate (1:2 molar ratio) | chlorpheniramine isostearate (1:2 molar ratio) |
|---|---|---|---|
| Erythema Rating | 2.0 | 1.3 | 1.7 |

Chlorpheniramine combined with myristic acid, palmitic acid or isostearic acid in the indicated molar ratios exhibited an irritancy rating that is less than that of uncomplexed chlorpheniramine alone or when dissolved uncomplexed in a fatty ester. However slight to well defined erythema is still observed.

f) Chlorpheniramine Combined with Stearic Acid in Increasing Molar Ratios

| Formulation | chlorphenir-amine stearate (1:1 molar ratio) | chlorphenir-amine stearate (1:2 molar ratio) | chlorphenir-amine stearate (1:3 molar ratio) |
|---|---|---|---|
| Erythema Rating | 3.1 | 2.0 | 1.2 |

Increasing amounts of saturated fatty acid in the chlorpheniramine formulation resulted in decreasing degrees of erythema compared to the uncomplexed amine base alone (see Example 6a) or when the uncomplexed amine dissolved in a fatty ester (see Example 6b).

g) Chlorpheniramine Combined with Oleic Acid, Undecylenic Acid, Linoleic Acid, and Octenoic Acid.

Chlorpheniramine formulations were prepared with one mole of chlorpheniramine and 1, 2 or 3 moles of undecylenic acid; 1 mole of chlorpheniramine and 1, 1.25, 1.5, 2, and 3 moles of oleic acid; 1 mole of chlorpheniramine and 1 mole of linoleic acid; and 1 mole of cchlorpheniramine and 2 moles of octenoic acid. The results are provided below.

| Formulation | chlorphenir-amine undecylenate (1:1 molar ratio) | chlorphenir-amine undecylenate (1:2 molar ratio) | chlorphenir-amine undecylenate (1:3 molar ratio) | | |
|---|---|---|---|---|---|
| Erythema Rating | 1.5 | 0.5 | 0.2 | | |
| Formulation | chlor-phenir-amine oleate (1:1 molar ratio) | chlor-phenir-amine oleate (1:1.25 molar ratio) | chlor-phenir-amine oleate (1:1.5 molar ratio) | chlor-phenir-amine oleate (1:2 molar ratio) | chlor-phenir-amine oleate (1:3 molar ratio) |
| Erythema Rating | 1.6 | 2.0 | 1.3 | 0.6 | 0 |

| Formulation | chlorpheniramine linoleate (1:1 molar ratio) | chlorpheniramine octenoate (1:2 molar ratio) |
|---|---|---|
| Erythema Rating | 1.3 | 0.33 |

The combination of chlorpheniramine with the unsaturated fatty acids indicated above resulted in an unexpected reduction in erythema scores when compared to the uncomplexed amine (Example 6a), with the uncomplexed amine dissolved in a fatty ester (Example 6b), or with the amine combined with a saturated fatty acid (Example 6f). In addition, increasing mole ratios of unsaturated fatty acid resulted in further minimization of erythema scores.

h) Hydroxyzine Combined with Oleic acid and Undecylenic acid.

Formulations were made consisting of 1 mole of hydroxyzine and 1, 2, or 3 moles of undecylenic acid, and I mole of hydroxyzine and 1, 2, or 3 moles of oleic acid. The results are provided below.

| Formulation | hydroxyzine undecylenate (1:1 molar ratio) | hydroxyzine undecylenate (1:2 molar ratio) | hydroxyzine undecylenate (1:3 molar ratio) |
|---|---|---|---|
| Erythema Rating | 0.2 | 0.2 | 0.2 |
| Formulation | hydroxyzine oleate (1:1 molar ratio) | hydroxyzine oleate (1:2 molar ratio) | hydroxyzine oleate (1:2 molar ratio) |
| Erythema Rating | 0.2 | 0.2 | 0.2 |

The combination of hydroxyzine with unsaturated fatty acids resulted in an unexpected reduction in erythema scores when compared to uncomplexed hydroxyzine dissolved in a fatty ester. Increasing mole ratios of the unsaturated fatty acids resulted in negligible or unremarkable erythema.

i) Diphenhydramine

| Formulation | Diphen-hydramine in 25% IPM | Diphen-hydramine Stearate (1:2) | Diphen-hydramine Undecyle-nate (1:2) | Diphen-hydramine Oleate (1:2) |
|---|---|---|---|---|
| Erythema Rating | 3.5 | 0 | 0 | 0.5 |

Diphenhydramine base in isopropyl myristate (IPM) was a severe skin irritant. The combination of diphenhydramine with various fatty acids in a 1 to 2 molar ratio reduced or eliminated erythema.

j) Chlorpheniramine Undecylenate (1:2 molar ratio) in Isopropyl Oleate or Isopropyl Myristate

| Formulation | Chlorpheniramine undecylenate (1:2 molar ratio) in isopropyl myristate | Chlorpheniramine undecylenate (1:2 molar ratio) in isopropyl oleate |
|---|---|---|
| Erythema Rating | 0.2 | 0.3 |

Chlorpheniramine undecylenate (1:2 molar ratio) at 33% by weight of the formulation with either the isopropyl oleate or isopropyl myristate at 67 % by of the formulation was evaluated for irritancy as described above. These chlorpheniramine fatty acid formulations dissolved in various fatty esters exhibited negligible erythema. These formulations were found to diffuse though human skin in vitro at flux rates that exceeded the uncomplexed chlorpheniramine flux rate.

k) Water Soluble Carboxylic Acid Salts of Chlorpheniramine

| Formulation | Chlorpheniramine maleate (1:1 molar ratio) | Chlorpheniramine salicylate (1:1 molar ratio) |
|---|---|---|
| Erythema Rating | 0.0 | 0.0 |

The water soluble salts of chlorpheniramine exhibited no skin irritation. However, these formulations are not useful because they do not penetrate the skin very effectively. The water soluble salts of chlorpheniramine are completely insoluble in fatty esters, furthermore, and would be expected to have a negligible flux in these solvents.

l) Erythema Associated with Unsaturated Fatty Acids

| Formulation | Undecylenic acid | Oleic acid | Linoleic acid |
|---|---|---|---|
| Erythema Rating | 0 | 0 | 0 |

The unsaturated fatty acids used in these formulations are not primary irritants or erythema causing agents.

m) Erythema Associated with Fatty Esters

| Formulation | isopropyl oleate | isopropyl myristate | propyl oleate | butyl stearate |
|---|---|---|---|---|
| Erythema Rating | 0 | 0.3 | 0 | 0 |

The fatty esters used in these formulations are not primary irritants or erythema causing agents.

Example 7 Transdermal Flux Rate of Chlorpheniramine (CP) in Isopropyl Oleate (IPO)

The transdermal flux rate of uncomplexed chlorpheniramine in 25 % (wt/wt), 50 %, and 75% isopropyl oleate was evaluated using the method set out in Section II above. The results are provided below in Table 3 and illustrated in FIG. 1. The lowest concentration of uncomplexed chlorpheniramine in isopropyl oleate (25%) yielded the highest flux rate. All of these formulations are severe skin irritants due to the absence of fatty acid in the composition.

TABLE 3

| Formulation | Flux ($\mu g/cm^2/hr$) |
|---|---|
| 100% Chlorpheniramine | 39.5 |
| 75% CP-25% IPO | 47.8 |
| 50% CP-50% IPO | 54.68 |
| 25% CP-75% IPO | 55.3 |

Example 8 Transdermal Flux Rate of Chlorpheniramine (CP) in Isopropyl Myristate

FIG. 2 is a graph of the transdermal flux through human skin in micrograms per centimeter$^2$ per hour of varying combinations of chlorpheniramine, undecylenic acid and isopropyl myristate, as indicated in Table 4 below. The 8.5% concentration of chlorpheniramine undecylenate (1 to 2 molar ratio) in a formulation with 79.7% IPM yielded an unexpected optimal transdermal flux rate that exhibits negligible irritancy.

TABLE 4

| Chlorpheniramine Undecylenate in Isopropyl Myristate | | | | | | |
|---|---|---|---|---|---|---|
| % Chlorpheniramine base | 2.1 | 8.5 | 20.4 | 31.2 | 42.3 | 100 |
| % Undecylenic acid | 2.6 | 11.7 | 28 | 42.7 | 57.7 | 0 |
| % Isopropyl myristate | 95.4 | 79.7 | 51.7 | 26.1 | 0 | 0 |
| Flux ($\mu g/cm2/hr$) | 4.8 | 53.6 | 39.6 | 17.8 | 4.8 | 39.5 |

Example 9 Transdermal Flux Rate of Chlorpheniramine (CP) Undecylenate in Isopropyl Oleate (IPO)

FIG. 3 is a graph of the transdermal flux through human skin in micrograms per centimeter per hour of varying combinations of chlorpheniramine, undecylenic acid and isopropyl oleate, as indicated in Table 5 below.

TABLE 5

| Chlorpheniramine Undecylenate in Isopropyl Oleate | | | |
|---|---|---|---|
| Chlorpheniramine (percent by weight) | % undecylenic acid | % IPO | Flux ($\mu g/cm2/hr$) |
| 2.1 | 2.9 | 95.0 | 17.4 |
| 6.5 | 8.9 | 84.6 | 40.7 |
| 12.7 | 17.1 | 70.2 | 43.5 |
| 14.0 | 18.8 | 67.0 | 27.3 |
| 27.3 | 36.9 | 35.0 | 12.9 |
| 42.3 | 57.7 | 0.0 | 11.1 |
| 100.0 | 0.0 | 0.0 | 39.5 |

The formulations containing between 6.5% and 12.7% chlorpheniramine undecylenate (1 to 2 molar ratio) in IPO yielded an unexpected optimal flux that exhibits negligible irritancy.

Example 10 Nicotine Isostearic Acid Complex

FIG. 4 is a graph of the transdermal flux rate through human skin in micrograms per centimeter per hour of the 1:2 molar ratio salt of nicotine and isostearic acid in isopropyl myristate.

TABLE 6

| 1:2 Nicotine Isostearic Acid Complex | | | | | | | |
|---|---|---|---|---|---|---|---|
| % Isopropyl Myristate | 95 | 75 | 50 | 62 | 25 | 0 | 0 |
| % Nicotine | 1.1 | 5.5 | 11 | 13.64 | 16.5 | 22 | 100 |
| % Isostearic Acid | 3.9 | 19.5 | 39 | 24.36 | 58.5 | 78 | 0 |
| Transdermal Flux ($\mu g/cm^2/hr$) | 13.83 | 57.48 | 108.1 | 120.4 | 104.4 | 58.13 | 75.65 |

Example 11 Dexbrompheniramine Undecylenate in Isopropyl Myristate

FIG. 5 is a graph of the transdermal flux through human skin in micrograms per centimeter$^2$ per hour of the dexbrompheniramine and undecylenic acid in a 1 to 2 molar ratio in varying amounts of isopropyl myristate, as indicated in Table 7 below. Dexbrompheniramine undecylenate in isopropyl myristate yields an unexpected optimal flux at 9.3% dexbrompheniramine salt.

TABLE 7

| Dexbrompheniramine Undecylenate in Isopropyl Myristate | | | |
|---|---|---|---|
| | 5% Dexbrompheniramine Undecylenate in IPM | 20% Dexbrompheniramine Undecylenate in IPM | 100% Dexbrompheniramine |
| Dexbrompheniramine | 2.32 | 9.3 | 46.4 |
| Undecylenic acid | 2.68 | 10.7 | 53.6 |
| Isopropyl Myristate | 95 | 80 | 0 |
| Flux ($\mu g/cm^2/hr$) | 4.1 | 23 | 3.9 |

Example 12 Diphenylhydramine Undecylenate in Isopropyl Myristate

FIG. 6 is a graph of the transdermal flux through human skin in micrograms per centimeter$^2$ per hour of diphenhydramine and undecylenic acid (1 to 1 molar ratio) in varying amounts of isopropyl myristate, as set out in Table 8 below.

TABLE 8

| Diphenhydramine Undecylenate in Isopropyl Myristate | | | | |
|---|---|---|---|---|
| | 25% Diphenhydramine salt | 50% Diphenhydramine salt | 75% Diphenhydramine salt | 100% Diphenhydramine salt |
| Diphenhydramine | 14.5 | 29 | 43.6 | 58 |
| Undecylenic acid | 10.5 | 21 | 31.4 | 42 |
| Isopropyl Myristate | 75 | 50 | 25 | 0 |
| Flux ($\mu g/cm^2/hr$) | 18.4 | 55.8 | 23 | 6 |

Example 13 Diphenhydramine Linoleic Acid

A salt of diphenhydramine was prepared by stirring it with an equimolar quantity of linoleic acid and was found to be non-irritating by the patch test. Samples of the salt were mixed with varying amounts of isopropyl myristate, as indicated in Table 9, and transdermal flux evaluated.

TABLE 9

| Diphenhydramine | | Linoleic Acid | | Isopropyl Myristate | | Base:Acid molar ratio | Flux mg/cm$^2$/hr |
| --- | --- | --- | --- | --- | --- | --- | --- |
| wt % | mole | wt % | Mole % | wt % | mole % | | |
| 12.0 | 12.7 | 13.2 | 12.7 | 74.8 | 74.6 | 1:1 | 21.0 |
| 23.7 | 25.0 | 26.0 | 25.0 | 50.3 | 50.0 | 1:1 | 61.8 |
| 35.5 | 37.3 | 39.0 | 37.3 | 25.5 | 25.4 | 1:1 | 29.2 |

The flux determined for the salt in the absence of solvent was 6.0 mg/cm2/hr.

VIII. Preparation of Transdermal Patch

Methods for preparing transdermal patches are known to those skilled in the art. For example, see Brown, L., and Langer, R., Transdermal Delivery of Drags, Annual Review of Medicine, 39:221–229 (1988), incorporated herein by reference.

Transdermal administration of an effective amount of a physiologically active nonionized amine requires that the formulation be maintained in contact with the skin for a prolonged period of time. This can be accomplished, for example, by thickening the solution to the point that it does not readily flow and approaches a solid in properties, either by appropriate selection of solvent or by adding appropriate thickeners or gelling agents to the solution. It can also be accomplished by dispersing into the organic solution an aqueous medium to form a very viscous or gel-like water-in-oil emulsion or slurry. L. Shargel, Pharmacy Review, Harwal Publishing Company, Media, PA, 1989 pp 34–43, incorporated herein by reference. The substantially non-flowing solution can simply be applied to or coated on the skin. In a preferred embodiment, a mechanical protection in the form of a cover or bandage is provided to prevent it from being wiped off. Another method for maintaining contact between the solution and the skin is to compound the solution with a suitable inert adhesive to produce a semisolid adhesive layer combining in one component the required payload of amine salt, the nonpolar diluent, and dermal adhesive properties. Such an adhesive layer can usefully be backed with a nonpermeable covering such as foil or plastic film to confine the drug and avoid adhesion to other surfaces. The organic solution can also be maintained in place by imbibing or absorbing it in a suitable solid carrier such as an absorbent pad of fibrous material or a porous water-insoluble polymeric matrix, the latter being preferred. It is particularly advantageous to incorporate the drug solution in a gelled cellulose triacetate matrix, as described, for example, in U.S. Pat. No. 3,846,404, incorporated herein by reference. In general, suitable carriers are porous, preferably microporous, water-insoluble materials throughout which the amine solution can be distributed or dispersed so that a supply of the amine is maintained in contact with the skin. In a preferred embodiment the carrier is provided with means for maintaining it in contact with the skin, such as a layer of adhesive. The adhesive may extend only along part or all of the periphery of the face of the carrier, or it may, if it is sufficiently permeable, cover the skin contacting face of the carrier. Goodman & Gilman, The Pharmacological Basis of Therapeutics, A. G. Goodman, T. W. RAll, A. S. Nies, P. Taylor, Editors, Pergamon Press 8$^{th}$ Edition, New York 1990. In the simplest case, a separate strip of adhesive tape may be employed to maintain the carrier in place. Among suitable carriers are absorbent paper, fibrous batts such as cotton batting, and various porous or microporous polymeric gel compositions such as partially cross-linked polyvinyl alcohol, polyvinyl pyrrolidone, or polyacrylamide and porous or microporous gels of cellulose esters or ethers including cellulose acetate, cellulose butyrate, cellulose nitrate, and the like. Particularly preferred is microporous cellulose triacetate gel, as pointed out above.

The rate of transport of the amine through the skin, hence the systemic-concentration level of the amine, can be adjusted by varying the area of the skin with which the solution is in contact, as pointed out above, or by varying the type and amount of fatty acid and/or solvent present, while the length of time during which a desired level of concentration is maintained can be adjusted by varying the amount of amine present. Brown, L., and Langer, R., Transdermal Delivery of Drugs, Annual Review of Medicine, 39:221–229 (1988).

Modifications and variations of the present invention will be obvious to those skilled in the art from the foregoing detailed description of the invention. Such modifications and variations are intended to come within the scope of the appended claims.

We claim:

1. A composition for the transdermal or topical administration of physiologically active amine that is irritating to humans, comprising:
   (1) a salt of the irritating amine, prepared by combining the amine with a stoichiometric molar excess of a fatty acid of from 8 to 22 carbon atoms wherein the molar ratio of irritating amine to fatty acid is one mole of amine at least 2 moles of fatty acid,
   (2) in a solvent consisting essentially of one or a mixture of nonpolar, nonvolatile solvents; wherein the term irritating physiologically active amine refers to an amine that obtains an irritation rating in humans of:
      (i) greater than 3 using Procedure A and a scoring system of 1 (no discoloration, no erythema), 2 (pink coloration, slight erythema), 3 (reddening, moderate erythema), 4 (reddening and burning, moderate erythema), 5 (erythema and edema, with or without burning, 6 (severe erythema, edema, and burning), and 7 (severe erythema, severe burning, blistering, and edema);
      (ii) or a score of 2 or greater using Procedure B and a scoring system of:

| ERYTHEMA AND ESCHAR FORMATION | Score |
| --- | --- |
| No erythema | 0 |
| Very slight erythema (barely perceptible) | 1 |
| Well defined erythema | 2 |
| Moderate to servere erythema | 3 |
| Severe erythema (beet readness) to slight eschar formation (injuries in depth) | 4 | and wherein the amount of the nonpolar, nonvolatile solvent is such that the transdermal flux rate of the salt of the amine, when applied to human skin in the solvent, is at least 50% that of the uncomplexed, unsolvated physiologically active amine.

2. The composition of claim 1, wherein the composition can be used to administer to a human in need thereof an effective dosage of the amine in a transdermal patch of no greater than approximately 25 cm$^2$.

3. The composition of claim 1, wherein the fatty acid is an unsaturated fatty acid.

4. The composition of claim i in which the solvent is selected from the group consisting of mineral oil, fatty esters, and fatty alcohols.

5. The composition of claim 1, wherein the physiologically active amine is dexchlorpheniramine.

6. The composition of claim 1, wherein the solvent is selected from the group consisting of mineral oil, isopropyl myristate, isopropyl oleate, propyl oleate, butyl stearate, methyl stearate, isocetyl stearate, butyl acetate, butyl myristate, cetearyl octanoate, cetyl palmitate, cetyl stearate, decyl oleate, diisopropyl adipate, dioctyl adipate, glyceryl oleate, isobutyl stearate, tributyl stearate, isocetyl stearate, isodecyl oleate, isopropyl isostearate, isopropyl lanolate, isopropyl linoleate, isopropyl stearate, myristyl lactate, myristyl myristate, myristyl stearate, octyl palmitate, octyl stearate, retinyl palmitate, isostearyl myristate, diethyl maleate, ethyl laurate, propylene glycol, and glyceridacid.

7. The composition of claim 1, wherein the transdermal flux rate is at least 70% that of the uncomplexed, unsolvated physiologically active amine.

8. The composition of claim 1, wherein the transdermal flux rate is at least equal to that of the uncomplexed, unsolvated physiologically active amine.

9. The composition of claim 1, wherein the physiologically active amine is selected from the group consisting of chlorpheniramine, dexchlorpheniramine, brompheniramine, and dexbrompheniramine.

10. An article adapted to be maintained in contact with human skin to administer an effective amount of physiologically active amine that is irritating to humans, comprising:
the composition of claim 1 absorbed in a solid, porous water-insoluble carrier.

11. The article of claim 9 in which the carrier comprises a polymeric matrix.

12. The article of claim 11 in which the polymeric matrix comprises cellulose triacetate.

13. The article of claim 9 wherein the surface contact with the skin is 25 cm$^2$ or smaller.

14. The article of claim 9, wherein the fatty acid is an unsaturated fatty acid.

15. The article of claim 9 in which the solvent is selected from the group consisting of mineral oil, fatty esters, and fatty alcohols.

16. The article of claim 9, wherein the physiologically active amine is dexchlorpheniramine.

17. The article of claim 9, wherein the solvent is selected from the group consisting of mineral oil, isopropyl myristate, isopropyl oleate, propyl oleate, butyl stearate, methyl stearate, isocetyl stearate, butyl acetate, butyl myristate, cetearyl octanoate, cetyl palmitate, cetyl stearate, decyl oleate, diisopropyl adipate, dioctyl adipate, glyceryl oleate, isobutyl stearate, tributyl stearate, isocetyl stearate, isodecyl oleate, isopropyl isostearate, isopropyl lanolate, isopropyl linoleate, isopropyl stearate, myristyl lactate, myristyl myristate, myristyl stearate, octyl palmitate, octyl stearate, retinyl palmitate, isostearyl myristate, diethyl maleate, ethyl laurate, propylene glycol, and glyceridacid.

18. The composition of claim 3, wherein the fatty alcohol is selected from the group consisting of dodecyl alcohol, stearyl alcohol, oleyl alcohol, ocacosyl alcohol, isopentyl alcohol, isooctyl alcohol, crotonyl alcohol decyl alcohol, octyl alcohol, and undecanol.

19. The article of claim 18, wherein the fatty alcohol is selected from the group consisting of dodecyl alcohol, stearyl alcohol, oleyl alcohol, ocacosyl alcohol, isopentyl alcohol, isooctyl alcohol, crotonyl alcohol, decyl alcohol, octyl alcohol, and undecanol.

20. A method for the transdermal or topical administration of an irritating physiologically active amine to a human, comprising providing an effective amount of a salt of the amine, prepared by combining the amine with fatty acid of from 8 to 22 carbon atoms in a solvent consisting essentially of one or a mixture of nonpolar, nonvolatile solvents wherein the ratio of irritating amine to fatty acid is one mole of amine to at least two moles of fatty acid wherein the term irritating physiologically active amine refers to an amine that obtains an irritation rating in humans of:
(i) greater than 3 using Procedure A and a scoring system of: 1 (no discoloration, no erythema), 2 .(.pink coloration, slight erythema), 3 (reddening, moderate erythema), 4 (reddening and burning, moderate erythema), 5 (erythema and edema, with or without burning), 6 (severe erythema, edema, and burning), and 7 (severe erythema, severe burning, blistering, and edema);
(ii) or a score of 2 or greater using Procedure B and a scoring system of:

| ERYTHEMA AND ESCHAR FORMATION | Score |
|---|---|
| No erythema | 0 |
| Very slight erythema (barely perceptible) | 1 |
| Well defined erythema | 2 |
| Moderate to servere erythema | 3 |
| Severe erythema (beet readness) to slight eschar formation (injuries in depth) | 4 | and wherein the amount of the nonpolar, nonvolatile solvent is such that the transdermal flux rate of the salt of the amine, when applied to human skin in the solvent, is at least 50% that of the uncomplexed, unsolvated physiologically active amine.

21. The method of claim 19, wherein the solvent is petrolatum.

22. The method of claim 19, wherein the amine salt is absorbed onto a solid, porous, water-insoluble carrier.

* * * * *